United States Patent
Li et al.

(10) Patent No.: US 11,759,423 B2
(45) Date of Patent: Sep. 19, 2023

(54) EXOSOME PREPARATION FOR TREATING DISEASE AND APPLICATION THEREOF

(71) Applicants: Li Li, Shanghai (CN); Xia Peng, Shanghai (CN); Guogang Xie, Shanghai (CN)

(72) Inventors: Li Li, Shanghai (CN); Xia Peng, Shanghai (CN); Guogang Xie, Shanghai (CN)

(*) Notice: Subject to any disclaimer, the term of this patent is extended or adjusted under 35 U.S.C. 154(b) by 576 days.

(21) Appl. No.: 16/479,561

(22) PCT Filed: Dec. 15, 2017

(86) PCT No.: PCT/CN2017/116608
§ 371 (c)(1),
(2) Date: Oct. 22, 2019

(87) PCT Pub. No.: WO2018/133602
PCT Pub. Date: Jul. 26, 2018

(65) Prior Publication Data
US 2020/0060970 A1    Feb. 27, 2020

(30) Foreign Application Priority Data
Jan. 20, 2017 (CN) .......................... 201710049857.6

(51) Int. Cl.
| | |
|---|---|
| A61K 9/127 | (2006.01) |
| A61P 37/06 | (2006.01) |
| A61P 37/08 | (2006.01) |
| A61K 35/15 | (2015.01) |
| C12N 5/0787 | (2010.01) |
| C12N 5/077 | (2010.01) |

(52) U.S. Cl.
CPC .......... *A61K 9/1271* (2013.01); *A61K 9/1277* (2013.01); *A61K 35/15* (2013.01); *A61P 37/06* (2018.01); *A61P 37/08* (2018.01); *C12N 5/0642* (2013.01); *C12N 5/0652* (2013.01)

(58) Field of Classification Search
None
See application file for complete search history.

(56) References Cited

U.S. PATENT DOCUMENTS

2013/0045236 A1* 2/2013 Fiebiger .................. A61P 29/00
422/69
2015/0093363 A1* 4/2015 Ekstrom ................ A61K 35/32
424/93.7

OTHER PUBLICATIONS

Karin Ekstrom et al. "Characterization of mRNA and microRNA in human mast cell-derived exosomes and their transfer to other mast cells and blood CD34 progenitor cells." Journal of Extracellular Vesicles, vol. 1, 2012, Article 18389, pp. 1-12. (Year: 2012).*

(Continued)

*Primary Examiner* — Isaac Shomer
(74) *Attorney, Agent, or Firm* — Wolf, Greenfield & Sacks, P.C.

(57) ABSTRACT

Provided are an exosome preparation formed by secretion by a mast cell cultured in vitro, a preparation method of an exosome therein, an exosome containing FcεRI protein on an outer surface thereof and in a substantially unbound state, and uses of the exosome preparation or exosome in a method for inhibiting mast cell activation in vitro and in preparing a drug for treating an IgE-mediated disease.

2 Claims, 2 Drawing Sheets

(56) References Cited

OTHER PUBLICATIONS

Dimitris Skokos et al. "Mast Cell-Derived Exosomes Induce Phenotypic and Functional Maturation of Dendritic Cells and Elicit Specific Immune Responses In Vivo." The Journal of Immunology, vol. 170, 2003, pp. 3037-3045. (Year: 2003).*

Karin Ekstrom. "Exosomal Shuttle RNA." Thesis, University of Gothenburg. https://gupea.ub.gu.se/bitstream/2077/9902/1/Thesis%20Karin%20Ekstr%c3%b6m.pdf on Nov. 1, 2021, originally published 2008, pp. 1-57. (Year: 2008).*

Dimitris Skokos, et al. "Mast Cell-Dependent B and T Lymphocyte Activation Is Mediated by the Secretion of Immunologically Active Exosomes." The Journal of Immunology, vol. 166, 2001, pp. 868-876. (Year: 2001).*

Medline Plus. "Omalizumab Injection." https://medlineplus.gov/druginfo/meds/a603031.html accessed May 24, 2022, pp. 1-6. (Year: 2022).*

Jian Gong, Ning-Sun Yang, Michael Croft, I-Chun Weng, Liangwu Sun, Fu-Tong Liu and Swey-Shen Chen. "The antigen presentation function of bone-marrow derived mast cells is spatiotemporally restricted to a subset of high levels of cell surface FcεRI and MHC II." BMC Immunology, vol. 11:34, pp. 1-13. (Year: 2010).*

International Search Report and Written Opinion for Application No. PCT/CN2017/116608, dated Mar. 16, 2018.

International Preliminary Report on Patentability for Application No. PCT/CN2017/116608, dated Aug. 1, 2019.

Li et al., Mast Cell-Derived Exosomes Promote Th2 Cell Differentiation via OX40L-OX40 Ligation. J Immunol Res. 2016;2016:3623898. doi: 10.1155/2016/3623898. Epub Mar. 15, 2016.

Ren et al., Negative signaling molecules of human mast cells and allergic diseases. Chinese Journal of Respiratory and Critical Care Medicine. Nov. 25, 2008;7(6):485-87.

Xiao, The Role of the Mast Cell Derived Exosome in Non-small Cell Lung Carcinomas. Shanghai Jiao Tong University School of Medicine. Doctoral Dissertation of Clinical Laboratory Diagnostics. Apr. 2014; 102 pages.

* cited by examiner

EXOSOME PREPARATION FOR TREATING DISEASE AND APPLICATION THEREOF

RELATED APPLICATIONS

This application is a national stage filing under 35 U.S.C. § 371 of International Application No. PCT/CN2017/116608, filed Dec. 15, 2017, and entitled "EXOSOME PREPARATION FOR TREATING DISEASE AND APPLICATION THEREOF," which claims the benefit of priority to Chinese application number CN 201710049857.6, filed Jan. 20, 2017, the contents of each application are incorporated herein by reference in their entirety.

TECHNICAL FIELD

The present invention relates to the field of biomedicine, and in particular to an exosome preparation for treating disease and application thereof.

BACKGROUND

Allergic diseases are typical IgE-mediated diseases. An epidemiological survey of allergic diseases in 30 countries by the World Allergy Organization (WAO) showed that about 22% of the population were affected by allergic diseases, and the number of cases increased year by year. The mechanism is: allergens enter the body for the first time to stimulate B lymphocyte to secrete the specific IgE, which binds to the IgE high affinity receptor FcεRIα present on mast cells and basophils (FcεRI is a tetramer composed of α, β, and two γ subunits, and the extracellular end of the α chain is a binding region of IgE), and the allergen can bind to the IgE on the surface of mast cells and basophils when it enters the body again, resulting in adjacent FcεRI cross-linking, causing activation of mast cells and basophils, releasing inflammatory mediators (histamines, leukotrienes, prostaglandins), cytokines and chemokine, leading to increased vascular permeability, angiotelectasis, smooth muscle contraction, increased glandular secretion, etc., causing local or systemic allergic conditions, including allergic rhinitis, asthma, conjunctivitis, eczema, food allergies, drug allergies and the like.

An autoimmune disease is a disease caused by the body's immune response to its own antigen, which causes damage to its own tissues. It involves many organs and tissues and covers hundreds of diseases, such as rheumatoid arthritis (RA), systemic lupus erythematosus (SLE), polymyositis/dermatomyositis, scleroderma, Sjogren syndrome (SS), etc. With the deep understanding of the immune system by scientists, the increase of detection methods and the improvement of diagnostic level, more and more autoimmune diseases are discovered. According to the statistics from the Association for Autoimmune Diseases, there are approximately 14.70-23.5 million patients with autoimmune diseases in the United States, up to 8% of the total population. It is the third major disease following the cardiovascular disease and cancer. In recent years, due to changes in people's living environment and living habits, the incidence of autoimmune diseases has increased year by year.

The production of autoantibodies is one of the important features for autoimmune diseases. Autoantibodies exist in most autoimmune patients. For example, the positive rate of anti-ds-DNA antibody in SLE patients exceeds 75%, and the positive rate of anti-SSA antibody in SS patients is also more than 75%. These antibodies may participate in the development and progression of autoimmune diseases by the following pathways: 1. interacting with cell surface receptors, altering the structure of the receptor or blocking the binding of the receptor to the corresponding ligand; 2. forming an immune complex that deposits in the blood vessels to cause tissue damage; 3. inducing cell lysis by complement-dependent cytotoxicity (CDC), antibody-dependent cell-mediated cytotoxicity (ADCC).

The traditional view is that most of the antibodies involved in these diseases are IgG type. In recent years, studies have shown that IgE-type autoantibodies also play an important pathogenic role in certain autoimmune diseases. In SLE patients, serum IgE anti-dsDNA autoantibodies are associated with the severity of the disease in patients, which can activate plasmacytoid dendritic cells (pDC) to secrete large amounts of IFN-γ, thereby aggravating the injury response in SLE patients. In addition, IgE of anti-ANA, anti-dsDNA, anti-BP230 and BP180 autoantibodies are also found in patients with RA, CSU and bullous pemphigoid (BP), which are closely related to the development of the disease.

Cardiovascular disease, also known as circulatory disease, is a group of heart and vascular diseases, including coronary heart disease, cerebrovascular disease, peripheral arterial vascular disease, rheumatic heart disease, congenital heart disease, deep vein thrombosis and pulmonary embolism. Cardiovascular disease is the leading cause of death worldwide. According to statistics, in 2012, 17.5 million people worldwide died of cardiovascular disease, accounting for 31% of the total number of deaths worldwide. Among them, 7.4 million people died of coronary heart disease and 6.7 million people died of stroke.

Coronary heart disease is the leading cause of death in cardiovascular disease, accounting for about more than 40% of deaths from cardiovascular disease. Coronary heart disease is such as disease that coronary artery vasospasm occur a atherosclerotic lesion that causes stenosis or obstruction of the vascular lumen, causing heart disease caused by myocardial ischemia, hypoxia or necrosis. There are five clinical types including asymptomatic myocardial ischemia (occult coronary heart disease), angina pectoris, myocardial infarction, ischemic heart failure (ischemic heart disease) and sudden death. The traditional view is that coronary heart disease is a simple lipid deposition disease. New research shows that coronary heart disease is closely related to inflammation. Many inflammatory factors and inflammatory cells (macrophages, neutrophils, mast cells, etc.) are accumulated in the plaque. The latest research has shown that allergic inflammation-related molecules (IgE) and cells (mast cells) are deposited in plaques and participate in the development of coronary heart disease. Serum IgE levels were elevated in patients with coronary heart disease, and IgE and its receptor FcεRI levels were also increased in plaques, and IgE levels were positively correlated with arterial stenosis in patients with coronary heart disease. Further studies have shown that IgE can promote the interaction of its high-affinity receptor FcεRI with TLR4 of other cells (macrophages and endothelial cells), thereby promoting the release of inflammatory molecules from macrophages, and inducing apoptosis of macrophages, endothelial cells, and smooth muscle cells and accelerating the formation of atherosclerotic plaques.

At present, IgE-mediated diseases are mainly allergic diseases, and the treatment for allergic diseases is still based on symptomatic treatment, including antihistamines, mast cell stabilizers (such as sodium cromoglycate, sodium hydroxy-propylcronate, etc.) and hormone drugs (i.e., immunosuppressive agents such as prednisone, dexamethasone, etc.). These drugs can only temporarily relieve allergic symptoms, once stopped, it is easy to relapse. Long-term medication should consider its side effects.

There is still no ideal method for the treatment of autoimmune diseases. Current treatment strategies include anti-inflammatory (corticosteroids, salicylic acid preparations, synthetic prostaglandin inhibitors), immunosuppression (cyclosporine A, FK-506), symptomatic treatment (insulin for type I diabetes patients, antithyroid drugs for hyperthyroidism, plasma exchange therapy for the severe illness). These methods can only alleviate the symptoms of the disease and it is difficult to cure the disease.

The treatment strategy for coronary heart disease mainly includes drug treatment (nitrates, calcium blocker, antiplatelet, anticoagulant or thrombolytics), interventional therapy and surgical treatment. Although different treatments have achieved significant effects, current drug treatment has limited effect on severe myocardial ischemia, and restenosis can occur at the surgical site or other sites of the coronary artery after interventional therapy (PCI) and coronary artery bypass grafting (CABG), which cannot cure coronary heart disease. Therefore, finding new therapeutic approaches has become an important topic in clinical research.

Therefore, there is an urgent need in the art to develop a new therapeutic approach that is effective in treating IgE-mediated related diseases.

SUMMARY OF INVENTION

The object of the present invention is to provide a new therapeutic approach that is effective in treating IgE-mediated related diseases.

In a first aspect of the present invention, it provides an exosome formulation comprising:

an exosome with a size of 30-100 nm, wherein the exosome is formed by the secretion of the cultured mast cells in vitro; and a pharmaceutically acceptable carrier.

In another preferred embodiment, the content (v/v) of the exosome in the formulation is 0.001 to 30%, preferably 0.05 to 15%, more preferably 0.1 to 10%, based on the total volume of the formulation.

In another preferred embodiment, the concentration of total protein in the exosome is from 0.01 to 10 mg/mL, preferably from 0.05 to 5 mg/mL, more preferably from 0.5 to 3.5 mg/mL; most preferably from 1 to 3 mg/mL.

In another preferred embodiment, the formulation is a liquid formulation, and/or a lyophilized powder formulation.

In another preferred embodiment, the dosage form of the formulation includes an injection, a spray, and/or a vernix.

In another preferred embodiment, the exosome contains an FcεRI protein located on the outer surface.

In another preferred embodiment, the source of the mast cells is selected from the group consisting of: primary mast cells (e.g., bone marrow-derived mast cells, umbilical cord blood-derived mast cells, tissue-derived mast cells), mast cell lines (LAD-2), basophils, basophilic cell line (KU812), FcεRIα expressing cells through transfection (e.g., pluripotent stem cells, mesenchymal stem cells, dendritic cells, Hela cells, 293T cells, HMC-1 cells and other primary cells and cell lines).

In another preferred embodiment, the pharmaceutically acceptable carrier is selected from the group consisting of phosphate buffer, physiological saline, trehalose solution, and a combination thereof.

In another preferred embodiment, the formulation further contains albumin.

In another preferred embodiment, the albumin has a content (v/v) of 0.5 to 50%, preferably 2.5 to 25%, more preferably 5-15% in the formulation on the basis of the total volume of the formulation.

In another preferred embodiment, the formulation contains 0.003-1% by weight, preferably 0.015-0.5% by weight, more preferably 0.03-0.35% by weight of exosome on the basis of the total weight of the formulation.

In another preferred embodiment, the formulation contains from 0.1 to 10% by weight, preferably from 0.5 to 5% by weight, more preferably from 1 to 3% by weight of albumin on the basis of the total weight of the formulation.

In another preferred embodiment, the weight ratio of exosome to albumin in the formulation is 1-10:10-1, preferably 1-5:5-1, more preferably 1-2: 2-1.

In a second aspect of the present invention, it provides an exosome comprising an FcεRI protein located on an outer surface, wherein the exosome has a size of 30-100 nm, and the exosome is formed by the secretion of the cultured mast cells in vitro, and the FcεRI protein is substantially in an unbound state.

In another preferred embodiment, the "substantially" means that ≥60%, ≥70%, ≥80%, ≥90% ≥95%, ≥98% or almost 100% of the FcεRI protein is in an unbound state.

In another preferred embodiment, the "in an unbound state" means that the FcεRI protein does not form a "FcεRI protein-IgE" complex with IgE.

In another preferred embodiment, the source of the mast cells is selected from the group consisting of primary mast cells (e.g., bone marrow-derived mast cells, umbilical cord blood-derived mast cells, tissue-derived mast cells), mast cell lines (LAD-2), basophils, basophilic cell line (KU812), FcεRIα expressing cells through transfection (e.g., pluripotent stem cells, mesenchymal stem cells, dendritic cells, Hela cells, 293T cells, HMC-1 cells and other primary cells and cell lines).

In a third aspect of the present invention, it provides a use of the exosome according to the second aspect of the present invention for the preparation of a medicament for a IgE-mediated related disease.

In a fourth aspect of the present invention, it provides a use of a formulation according to the first aspect of the present invention for the preparation of a medicament for the treatment of a IgE-mediated related disease.

In another preferred embodiment, the IgE-mediated related disease is selected from the group consisting of an allergic disease, an autoimmune disease, a cardiovascular disease, a nephrotic syndrome, and a combination thereof.

In another preferred embodiment, the allergic disease is selected from the group consisting of an allergic asthma, an allergic rhinitis, an atopic dermatitis, an allergic conjunctivitis, a systemic allergic reaction, a food allergy, a drug allergy, and a combination thereof.

In another preferred embodiment, the autoimmune disease is selected from the group consisting of a systemic lupus erythematosus, a rheumatoid arthritis, a bullous pemphigoid, a scleroderma, a mixed connective tissue disease, a Hashimoto's thyroiditis, a ulcerative colitis, and a combination thereof.

In another preferred embodiment, the cardiovascular disease is selected from the group consisting of an acute myocardial infarction, a stable angina pectoris, an unstable angina pectoris, an acute coronary syndrome, a calcified aortic valve disease, and a combination thereof.

In another preferred embodiment, the medicament is further for one or more uses selected from the group consisting of:

(i) the neutralization of serum free IgE;

(ii) the inhibition of the binding of IgE to FcεRI on the surface of mast cells;

(iii) the inhibition of the activation of mast cells.

In another preferred embodiment, the inhibition of the activation of mast cells comprises decreasing one or more indicators selected from the group consisting of: □β-hexosidase release rate, histamine release rate, 5-hydroxy tryptamine, tryptase, chymotrypsin, prostaglandin, leukotrienes, cytokines (IL-6, IL-4, IL-5).

In a fifth aspect of the present invention, it provides a non-therapeutic method for inhibiting the activation of mast cell in vitro, comprising the steps of:

in the presence of the exosome formulation according to the first aspect of the present invention or the exosome according to the second aspect of the present invention, culturing the mast cell to inhibit the activation of mast cell.

In another preferred embodiment, the concentration of the exosome is 0.011-21000 μg/mL, preferably 0.0210-1500 μg/mL, more preferably 0.250-0.6200 μg/mL.

In another preferred embodiment, the mast cell is from a human or a non-human mammal.

In another preferred embodiment, the non-human mammal is a rodent or primate, preferably comprising a mouse, a rat, a guinea pig, a rabbit, and/or a monkey.

In a sixth aspect of the present invention, it provides a method for preparing an exosome, comprising the steps of:

(i) providing an in vitro culture system comprising a bone marrow-derived mast cell and a medium suitable for the growth of the cell, and the culture system further comprises 0.1-5 mmol/L of L-glutamine, 0.1-5 mmol/L of sodium pyruvate, and 5-15% of (v/v) fetal bovine serum without the exosome;

(ii) culturing it for 1-5 days under conditions suitable for the growth to obtain a culture product;

(iii) isolating the exosome according to the second aspect of the present invention from the culture product.

In another preferred embodiment, in the culture system of the step (i), the concentration of the bone marrow-derived mast cell is $1 \times 10^5$-$1 \times 10^7$/ml.

In another preferred embodiment, in step (ii), the culture is carried out at 37±1° C.

In a seventh aspect of the present invention, it provides a method of treating an IgE-mediated related disease, comprising the steps of:

administering an exosome formulation according to the first aspect of the present invention to a subject in need of treatment.

In another preferred embodiment, the subject comprises a human or a non-human mammal.

In another preferred embodiment, the subject comprises a rodent such as a mouse or a rat.

In another preferred embodiment, the exosome formulation is administered in an amount of from 0.01 to 5 mg/kg, preferably from 0.1 to 2 mg/kg, more preferably from 0.2 to 1 mg/kg of body weight.

It should be understood that, within the scope of the present invention, each technical feature of the present invention described above and in the following (as examples) may be combined with each other to form a new or preferred technical solution, which is not listed here due to space limitations.

DETAILED DESCRIPTION

Figure 1:
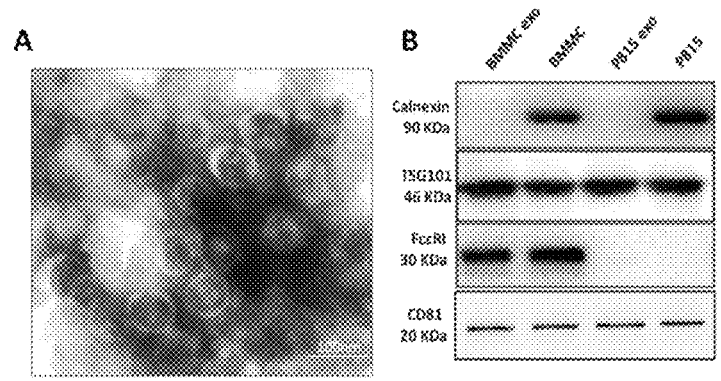
FIG. 1 shows: A. the exosome is a circular structure with a diameter of 50-80 nm under electron microscope; and B. Western blot shows the exosome expressing exosome characteristic molecule TSG101 protein and CD81 protein, and FcεRI was expressed on the BMMC cell and the exosome thereof, while FcεRI was not expressed on the P815 cell and the exosome thereof.

After an extensive and in-depth study, the present inventors have unexpectedly discovered that the mast cell cultured under specific conditions in vitro can secrete the specific exosome containing a very abundant FcεRI protein located on the surface, and the FcεRI protein is essentially in an unbound state. The FcεRI protein-containing exosome can competitively bind to IgE, thereby significantly inhibiting the binding of IgE to the mast cell, reducing the binding rate of IgE to the mast cell, thereby extremely effectively eliminating serum IgE. Furthermore, experiments have shown that the FcεRI protein-containing exosome of the present invention can also unexpectedly inhibit the activation of the mast cell and treat IgE-mediated related diseases such as allergic asthma. On this basis, the inventors complete the present invention.

As used herein, the terms "exosome", "FcεRI-exosome" can be used interchangeably and refer to an exosome containing an FcεRI protein located on the outer surface which is secreted by the mast cell cultured in vitro (preferably, the bone marrow-derived mast cell).

Exosome

Exosomes (exosome or vesicular body) are the membrane vesicles secreted by cells that carries certain surface molecules and contents of metrocytes (proteins, RNA, etc.) and are important mediators of signal transmission between cells. The exosome is widely distributed and has high biological activity and low immunogenicity, and is a microcosm of the cells from which it is derived. The use of the exosomes as carriers to deliver target molecules and drugs has become a hot topic in biotherapy and vaccine development in recent years.

The study has shown that mast cell-derived exosome carries various membrane receptors, ligands, adhesion molecules, costimulatory signaling molecules, and nucleic acid molecules (miRNAs and microRNAs) such as FcεRI and KIT, which may be an important way for mast cells to interact with other cells and membrane proteins.

In the present invention, based on the low immunogenicity of the exosome of the autologous mast cell, the FcεRI carried by the mast cell-derived exosome neutralizes the serum IgE, blocking the binding of IgE to IgE high affinity receptor FcεRI on the surface of mast cells and basophils, inhibiting the activation of the mast cell and alleviating the progression of the disease, which may be an effective way to treat IgE-related diseases.

Exosome Formulation

The exosome formulation of the present invention contains a safe and effective amount of an exosome together with a pharmaceutically acceptable carrier or excipient. Such carriers include, but are not limited to, saline, buffer, glucose, water, glycerol, ethanol, powders, and combinations thereof. The pharmaceutical formulation should be matched to the mode of administration.

In a preferred embodiment, the exosome is 30-100 nm in size and the exosome is secreted by cultured mast cells in vitro.

In a preferred embodiment, the formulation of the present invention may also contain a safe and effective amount of albumin which has the effect of stabilizing the formulation. Studies by the inventors have shown that the addition of a certain proportion of albumin can significantly improve the therapeutic effect and stability of the FcεRI-exosome of the present invention.

The pharmaceutical composition of the present invention can be formulated into a liquid formulation which can be prepared by a conventional method, and the liquid formulation is preferably prepared under aseptic conditions. The active ingredient is administered in a therapeutically effective amount, for example, from about 1 microgram per kilogram body weight to about 50 milligrams per kilogram body weight per day, from about 5 micrograms per kilogram body weight to about 10 milligrams per kilogram body weight, and about 10 micrograms per kilogram body weight to about 5 milligrams per kilogram body weight. In addition, the formulation of the present invention may also be used with other therapeutic agents.

When a formulation of the present invention is used, a safe and effective amount of the medicament is administered to the mammal, wherein the safe and effective amount is usually at least about 10 micrograms per kilogram of body weight, and in most cases no more than about 50 milligrams per kilogram of body weight, preferably, the dose is from about 10 micrograms per kilogram of body weight to about 20 milligrams per kilogram of body weight. Of course, specific doses should also consider factors such as the route of administration, the health of the patient, etc., which are all within the skill of a skilled physician.

Preparation Method of FcεRI-Exosome and the Formulation

In the present invention, cells expressing FcεRI on the surface (primary cultured mast cells, basophils, mast cell lines, basophils, other cells expressing FcεRI through transfection) are used as a source of the exosome. The formed exosome is isolated from the culture system by in vitro culture for a period of time (e.g., 1-5 days, preferably 1.5-3 days).

In the present invention, the formulation or pharmaceutical composition of the present invention can be obtained by mixing the prepared FcεRI-exosome with a pharmaceutically acceptable excipient.

In the present invention, a preferred formulation is a liquid FcεRI-exosome formulation.

Typically, a method of preparing an exosome formulation comprises the steps of:
1) preparing FcεRI-exosome by ultracentrifugation or Fibercell™ 3D hollow fiber cell culture system;
2) adding albumin to a medically acceptable solvent, the volume ratio of which is 0.5-50%;
3) adding the obtained exosome into a medically acceptable solvent in a volume ratio of 0.1-30% (V/V), and the content of the exosome is 0.03-10 mg/mL, thereby obtaining the exosome formulation.

Usage

The exosome containing unbound FcεRIα on the surface (FcεRI-exosome) prepared by the present invention can effectively neutralize free IgE in vivo, reduce binding of IgE to mast cell membrane receptor, thereby reducing mast cell degranulation and inhibiting allergic reaction, which can gradually reduce the number of mast cells and the expression of IgE receptors, thereby achieving the purpose of treating allergies and IgE-related diseases.

Typically, an exosome or an exosome formulation (or a corresponding drug) containing the exosome of the present invention can neutralize free IgE in vivo, reduce the binding of IgE to mast cell membrane receptors, thereby reducing mast cell degranulation and inhibiting allergy, thereby achieving the purpose of treating allergies and IgE-related diseases (such as allergic diseases (such as allergic asthma), autoimmune diseases, cardiovascular diseases).

The Main Advantages of the Present Invention Include:

(1) The FcεRI-exosome of the present invention is obtained by extracting from a cell culture supernatant, which is easy to be prepared and can be derived from autologous cells, and is non-immunogenic.

(2) The FcεRI-exosome of the present invention neutralizes the free IgE in the serum, and reduces the binding of IgE to FcεRI-positive cells, including mast cells, basophils, macrophages, etc., and can be used for IgE-mediated diseases, including allergies, autoimmune diseases, cardiovascular diseases, etc.

(3) The present invention discloses for the first time an exosome formulation containing FcεRI-exosome, which can effectively neutralize free IgE in the serum and reduce the binding of IgE to FcεRI-positive cells, thereby treating IgE-mediated related diseases.

(4) The present invention discloses for the first time an exosome formulation containing FcεRI-exosome, which can also reduce the expression level of FcεRI on the cell surface of mast cells, basophils, dendritic cells and the like, and reduce the activation of mast cells to treat IgE-mediated related diseases.

The present invention is further described below with reference to specific embodiments. It should be understood that these examples are only for illustrating the present invention and not intended to limit the scope of the present invention. The conditions of the experimental methods not specifically indicated in the following examples are usually in accordance with conventional conditions as described in Sambrook et al., Molecular Cloning: A Laboratory Manual (New York: Cold Spring Harbor Laboratory Press, 1989), or according to the conditions described in the Journal of Microbiology: An Experimental Handbook (edited by James Cappuccino and Natalie Sherman, Pearson Education Press) or the manufacturer's proposed conditions.

Unless otherwise stated, the materials used in the examples are all commercially available products.

Example 1 Preparation of FcεRI-Exosome

In this example, normal mouse bone marrow-derived mast cells (BMMC) were used as the source cells of the exosomes. Methods are shown as below: Bone marrow cells were extracted from the tibia and femur of mice (purchased from Shanghai Sippe-Bk Lab Animal Co., Ltd.), induced by interleukin 3 (IL-3) and stem cell factor (SCF) for 4 weeks, thereby obtaining the murine bone marrow derived mast cells.

The fetal bovine serum was taken, and the exosomes were removed by ultracentrifugation (100,000 g for 90 min) to obtain the serum without the exosomes.

Mouse bone marrow-derived mast cells and commercially available 1640 medium (added with a final concentration of 1 mmol/L glutamine and a final concentration of 1 mmol/L sodium pyruvate, and containing 10% of the serum without the exosomes) were mixed, and the cell concentration was adjusted to be $1\times10^6$/ml, and the mixture was cultured at 37° C. for 48 hours; the culture solution was collected, centrifuged at 300 g for 10 min, and the supernatant was retained, and the cell pellet was removed, and the cell debris was removed; the supernatant was centrifuged at 16500 g for 20 min and the supernatant was retained, and the cell pellets were removed, and the cell debris and apoptotic bodies were removed; the supernatant was centrifuged at 120,000 g for 90 min, and the supernatant was removed, and the pellet was collected, thereby obtaining the exosome, which was then resuspended in PBS buffer, and the protein concentration was measured with BCA kit.

The result is shown in FIG. 1. The results of electron microscopy show that the exosome is 30-100 nm and the total protein concentration is 3 mg/mL. In addition, almost 100% of the Fc ε RI protein is in an unbound state (i.e., the Fc ε RI protein is unbound).

Example 2 Preparation of FcεRI-Exosome Formulation

900 μL of physiological saline was added into 50 μL of 20% human albumin to a final mass concentration of 1% (wt/wt); and 50 μL of $4\times10^8$ cell-extracted exosome was added to obtain an exosome formulation. The absolute amount of total protein in the exosome was 2 mg.

Example 3 Binding Ability of FcεRI-Exosome to IgE

FcεRI-exosome (BMMC-extrasome) formulation and the FcεRI(−)-exosome (P815-exosome) formulation were prepared according to the methods of Example 1 and Example 2 using BMMC (FcεRI-expressing) and P815 cells (without expressing FcεRI) (purchased from ATCC) as the source cells of the exosomes.

The exosomes were incubated with IgE for 2 h and then was added to BMMC for incubation, and in the other group, BMMC-exosome and IgE were simultaneously added into BMMC for incubation. After incubation with each cells for each group, it was washed and the fluorescein isothiocyanate (FITC)-labeled anti-IgE antibody was added, and flow cytometry was used to detect the fluorescence of the surface of the BMMC.

Figure 2:
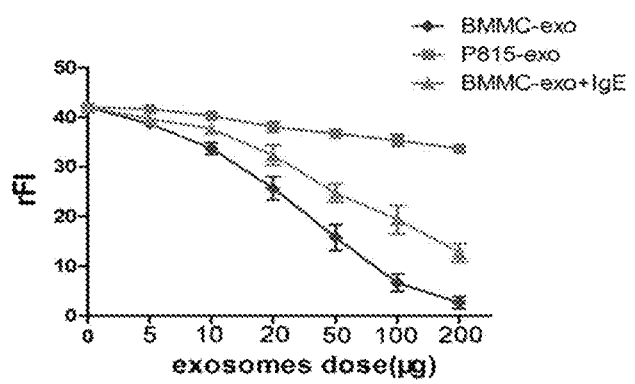
FIG. 2 shows the dose-effect relationship between the dose of the exosome and the relative fluorescence intensity (rFI) of BMMC. The red line shows the amount of IgE not bound to exosome detected by flow cytometry after different concentrations of P815-exosome (not expressing FcεRI) were pre-incubated with IgE for 2 h, then incubated with BMMC, and FITC-labeled anti-IgE antibody was added after washing. The blue line shows the remaining amount of IgE detected after different concentrations of BMMC-exosome (expressing FcεRI) were pre-incubated with IgE for 2 h. The green line shows the remaining amount of IgE detected after different concentrations of BMMC-exosome, IgE and BMMC were simultaneously incubated, and FITC-labeled anti-IgE antibody was added.

The result is shown in FIG. 2. The results show that BMMC-exosome can inhibit the binding of IgE to BMMC, and as the dose of BMMC-exosome increases, the binding rate of IgE to BMMC decreases, which is negatively correlated; however, P815-exosome has no significant effect on the binding rate of IgE and BMMC.

Example 4 FcεRI-Exosome Inhibits IgE-Mediated Mast Cell Activation

The effect of FcεRI-exosome on mast cell activation was examined using β-hexosidase release and histamine release assays.

FcεRI-exosome (BMMC-exo some) formulation was prepared according to Example 1 and Example 2, and BMMC-exosome (100 μg) was incubated with IgE for different time (0.5, 1, 2, 4 h), and then added to BMMC suspension, and incubated for 1 h at 37° C. for sensitization; after being washed, DNP-HSA (0.5 μg/ml) was added to stimulate, and the cell supernatant (A) was collected, and the cell pellet was lysed and the lysate was collected, and the supernatant (B) was obtained by centrifugation. The β-hexosidase and histamine concentrations were measured, and the release rate was calculated, and the release rate=A concentration×A volume/(A concentration×A volume+B concentration×B volume).

The results show that the release rates of the β-hexosidase and histamine of mast cells in the BMMC-exosome group have decreased compared with the non-BMMC-exosome group, and with the increase of the incubation time, the release rates of the β-hexosidase and histamine have decreased, indicating that BMMC-exosome can inhibit the activation of BMMC.

Example 5 FcεRI-Exosome Alleviates Allergic Asthma in Mice

An FcεRI-exosome (BMMC-exosome) formulation was prepared according to Example 1 and Example 2.

Construction of a mouse model of allergic asthma: the mice were sensitized by intraperitoneal injection of premixed OVA (20 μg) and the adjuvant aluminum hydroxide (4 mg) mixture on days 0, 7, and 14, and on the day 21, the 1% OVA solution was used for aerosol inhalation, 30 min/time/day, and continuous inhalation for 5 days.

Grouping: BALB/c mice (purchased from Shanghai Sippe-Bk Lab Animal Co., Ltd.) were randomly divided into 5 groups: control group (group A), asthma group (group B), treatment group for 1 month (group C), treatment group for 2 months (group D), and treatment group for 3 months (group E) respectively. Wherein in the control group, it was sensitized and stimulated with normal saline; in the asthma group, it was sensitized and stimulated with OVA; in the treatment group for one month, the inhalation was carried out with 1% OVA from day 32, 30 min/time/day, twice a week, and 40 μg/150 μL of BMMC-exosome was injected into the tail vein 30 minutes before the weekly stimulation for a total of 4 injections. In the treatment group for 2 months and the treatment group for 3 months, the treatment method was the same with that in the treatment group for 1 month, except that the number of injections was 8 and 12 times respectively.

Airway High Reactivity (AHR) was detected after the last stimulation of each group of mice; serum, bronchoalveolar lavage fluid (BALF) and lung tissues were collected to detect the number of inflammatory cells, the levels of inflammatory mediators, and pathological changes in lung tissue.

Figure 3:
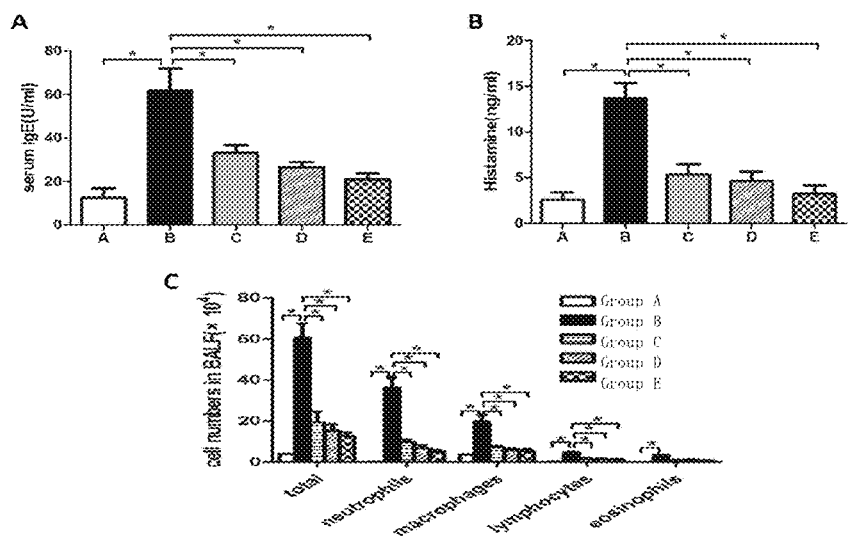
FIG. 3 shows the effect of BMMC-exosome on IgE (panel A), histamine (panel B) and leukocytes and their differential counts (panel C) in alveolar lavage fluid of allergic asthma mice. Among them, group a represents the control mice that is not sensitized and challenged; the mice in groups b-d are sensitized and challenged by OVA, wherein group b is given saline treatment, group c is given exosome for the treatment of one month, and group d is given exosome for the treatment of 2 months, group e is given exosome for the treatment of 3 months.
Figure 4:
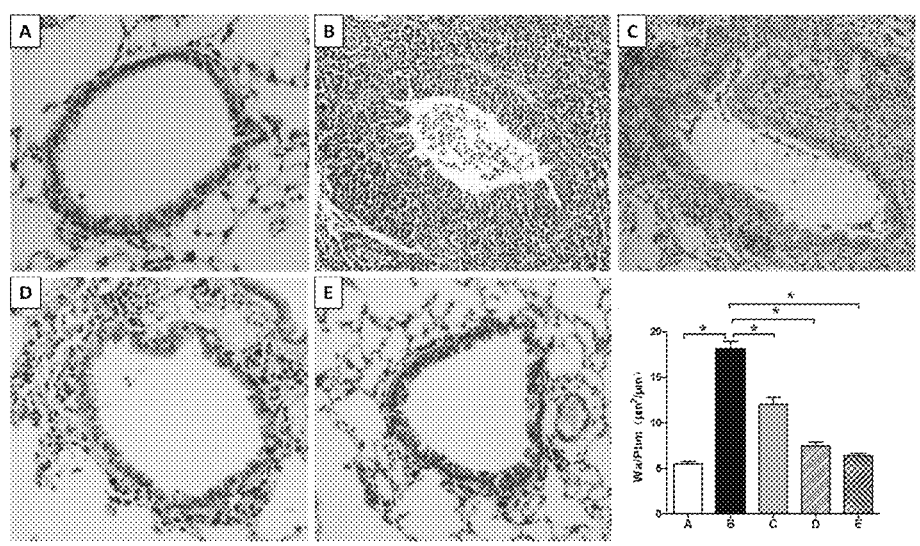
FIG. 4 shows the effect of BMMC-exosome on inflammatory cell infiltration in lung tissue of mice with allergic asthma. The lung tissue in mice is fixed by formaldehyde, embedded in paraffin, sectioned, HE stained. a represents lung tissue of control mice that is not sensitized and challenged; b represents lung tissue of allergic mice treated with saline, and c represents the lung tissue of allergic mice given exosome treatment for one month, and group d represents the lung tissue of allergic mice given exosome treatment for 2 months, and e represents the lung tissue of allergic mice given exosome treatment for 3 months.

The results are shown in FIGS. 3 and 4. The results show that BMMC-exosome can effectively improve AHR in asthmatic mice, reduce OVA-specific IgE (OVA-sIgE) levels in the serum of asthmatic mice, the number of inflammatory cells in BALF, and histamine and Th2 cytokines (IL-4, IL-5 and IL-13) levels, increase the secretion of anti-inflammatory factors (IL-10 and IFN-γ), and reduce the infiltration of inflammatory cells in the lung tissue, mucus secretion and proliferation of airway smooth muscle. Moreover, the effect of BMMC-exosome on the inhibition of allergic reactions increases with prolonged treatment time.

All publications mentioned herein are incorporated by reference as if each individual document was cited as a reference, as in the present application. It should also be understood that, after reading the above teachings of the present invention, those skilled in the art can make various changes or modifications, equivalents of which falls in the scope of claims as defined in the appended claims.

The invention claimed is:
1. A method of treating an IgE-mediated related disease, comprising:
administering an exosome formulation to a subject in need of treatment,
wherein:
the exosome formulation comprises an exosome with a size of 30-100 nm and a pharmaceutically acceptable carrier;
the exosome is formed by the secretion of cultured mast cells in vitro; and
the exosome contains an FcεRI protein located on the outer surface, wherein the IgE-mediated related disease is an allergic disease, and wherein the exosome is obtained by induction of 4 weeks with a combination of interleukin 3 (IL-3) and stem cell factor (SCF).

2. A method of treating an IgE-mediated related disease, comprising:
administering an exosome of to a subject in need of treatment,
wherein:
the exosome comprises an FcεRI protein located on an outer surface;
the exosome has a size of 30-100 nm;
the exosome is formed by the secretion of cultured mast cells in vitro; and
the FcεRI protein is substantially in an unbound state, wherein the IgE-mediated related disease is an allergic disease, and wherein the exosome is obtained by induction of 4 weeks with a combination of IL-3 and SCF.

* * * * *